United States Patent [19]

Graham et al.

[11] 4,173,631
[45] Nov. 6, 1979

[54] 7-METHYL-8-METHYLAMINO-10-(1'-D-RIBITYL)ISOALLOXAZINE

[75] Inventors: Donald W. Graham, Mountainside; Edward F. Rogers, Middletown, both of N.J.

[73] Assignee: Merck & Co., Inc., Rahway, N.J.

[21] Appl. No.: 911,619

[22] Filed: Jun. 1, 1978

Related U.S. Application Data

[63] Continuation-in-part of Ser. No. 716,498, Aug. 23, 1976, abandoned.

[51] Int. Cl.² .................... A61K 31/525; C07H 19/04
[52] U.S. Cl. ...................................... 424/180; 536/19
[58] Field of Search .......................... 424/180; 536/19

[56] References Cited

U.S. PATENT DOCUMENTS

| 2,825,729 | 3/1958 | Petering et al. | 536/19 |
| 3,052,668 | 9/1962 | Lambooy | 536/19 |
| 4,091,094 | 5/1978 | Graham et al. | 536/19 |

Primary Examiner—Johnnie R. Brown
Attorney, Agent, or Firm—Walter Patton; Harry E. Westlake, Jr.

[57] ABSTRACT

The novel compound 7-methyl-8-methylamino-10-(1'-D-ribityl)isoalloxazine is prepared. This compound has anticoccidial, antiprotozoal and antiparasitic activity. It is particularly useful for controlling cecal and/or intestinal coccidiosis when administered in minor quantities to animals, in particular to poultry, usually in admixture with animal sustenance.

7 Claims, No Drawings

7-METHYL-8-METHYLAMINO-10-(1'-D-RIBITYL) ISOALLOXAZINE

CROSS REFERENCE TO RELATED APPLICATIONS

This is a continuation-in-part application of co-pending application Ser. No. 716,498, filed Aug. 23, 1976 abandoned.

BACKGROUND OF THE INVENTION

This invention relates to a new chemical compound and the method for preparing the same. It relates further to the use of the new compound for treating and preventing coccidiosis. The compound of the present invention is also effective against protozoal infections especially against human and animal trypanosomiasis and against parasitic infections especially against malaria. This invention still more particularly relates to the novel compound 7-methyl-8-methylamino-10-(1'-D-ribityl)isoalloxazine and the use of the same in the control and treatment of coccidiosis.

Coccidiosis is a widespread poultry disease which is produced by infections of protozoa of the genus Eimeria which causes severe pathology in the intestines and ceca of poultry. Some of the most significant of these species are *E. tenella, E. acervulina, E. necatrix, E. brunetti* and *E. maxima*. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

Trypanosomiasis is a term used to describe a group of allied protozoal diseases, each of which is due to infection with a species of the genus Trypanosoma. They reach their greatest importance in Africa where their presence in enzootic form precludes the keeping of domestic animals throughout the largest part of the continent between 15° N and 20° S latitude. The pathogenic trypanosomes of Africa are considered to be primarily associated with the tsetse flies (glossina) which feed on vertebrate blood. Wherever tsetse are present, trypanosomiasis will also be found in some part of the mammalian population. The clinical findings are typically those of a wasting disease with intermittent fever. Anemia, edema, and cachexia are parts of the syndrome.

The important trypanosomes pathogenic to domestic animals are *T. congolense, T. simiae, T. vivax,* and *T. brucei*. The latter trypanosome is morphologically identical to *T. gambiense*, responsible for human "sleeping sickness" of Africa. A trypanosome found in the Western Hemisphere is *T. cruzi*, which affects both domestic animals and man.

Malaria is a serious parasitic infection normally transmitted by the bite of an infected anopheles mosquito, although it may also be produced by transfusion of blood from an infected donor. It is found most frequently in the tropics and in some tropical areas is hyperendemic. In man it is caused most frequently by the parasites *Plasmodium falciparum, P. vivax* and *P. malariae*. The acute phase of the disease is characterized by shaking chills, high fever sweats and headache. With malaria due to *P. vivax* and *P. malariae* the patient frequently suffers relapse because of the ability of these parasites to harbor in liver cells for extended periods of time. In view of the recurrent nature of the disease, chemotherapy is used not only to treat the acute phases, but also on an extended basis as a prophylactic or suppressive therapy. Although there are now available synthetic chemicals for the treatment of malaria, the search has continued for new and/or improved antimalarials and for compounds effective against strains of Plasmodia resistant to currently available agents.

SUMMARY OF THE INVENTION

This invention is based on the discovery that the novel compound 7-methyl-8-methylamino-10-(1'-D-ribityl)isoalloxazine has a surprisingly and unexpectedly high degree of activity against coccidiosis of poultry with respect to the structurally closely related 7-methyl-8-alkylamino-10-(1'-D-ribityl)isoalloxazines. Administering a small amount of this compound, preferably in combination with poultry feed, is effective in preventing or greatly reducing the incidence of coccidiosis. The compound is effective against both the cecal form (caused by *E. tenella*) and the intestinal forms (principally caused by *E. acervulina, E. brunetti, E. maxima* and *E. necatrix*).

The novel compound, 7-methyl-8-methylamino-10-(1'-D-ribityl)isoalloxazine, of this invention is prepared from the starting material, 8-chloro-7-methyl-10-(1'-D-ribityl)isoalloxazine (I). This starting material is disclosed in E. E. Haley et al., *J. Am. Chem. Soc.*, 76, 5093 (1954) which is herein incorporated by reference. The novel compound of the present invention is prepared by treating 8-chloro-7-methyl-10-(1'-D-ribityl)isoalloxazine with an excess of methylamine in a suitable solvent. The resulting solution is heated in a sealed tube until the reaction is complete. The reaction mixture is evaporated to dryness under reduced pressure and the residue is recrystallized to obtain pure 7-methyl-8-methylamino-10-(1'-D-ribityl)isoalloxazine (II). The process for preparing the novel compound of this invention is set forth in Table I below:

TABLE I

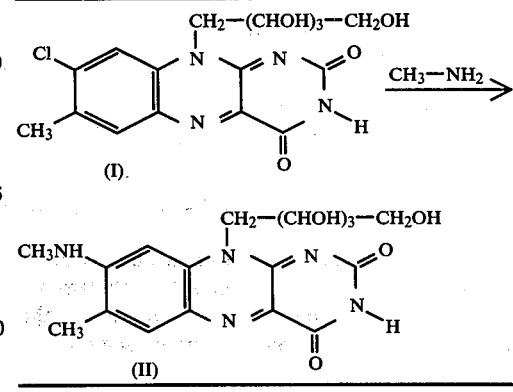

Alternately the coccidiostat of the present invention is prepared by the process for preparing 7-methyl-8-dimethylamino-10-(1'-D-ribityl)isoalloxazine (roseflavin), described in Kasai et al., *Bull. Chem. Soc. Japan,* 48, 2877-2880 (1975). The known compound 2- methylamino-p-toluidine, (III), is condensed with D-ribose, (IV), in refluxing methanol to give the ribose derivative, (V). The crude reaction mixture containing (V) is transferred to an autoclave and hydrogenated using Raney nickel as a catalyst to give the ribityl derivative, (VI). A methanolic solution of (VI) is poured into a hot methanolic solution of violuric acid and refluxed. Upon cooling, pure crystalline 7-methyl-8-methylamino-10-(1'-D-ribityl)-isoalloxazine, (II), is obtained. This process is set forth in Table II below:

TABLE II

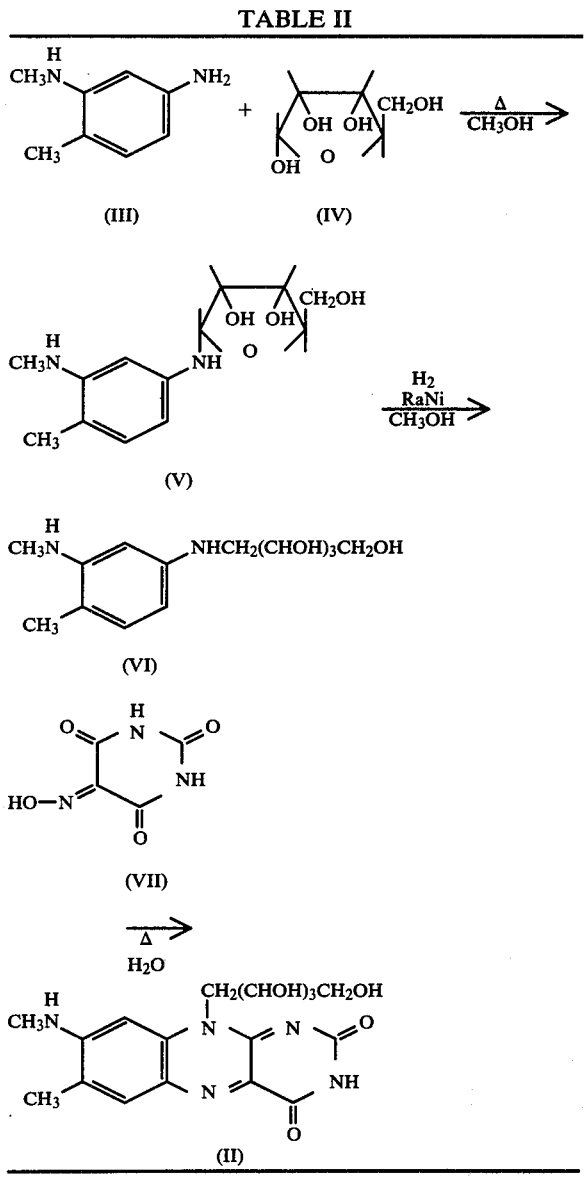

It is, therefore, a primary object of this invention to provide the novel compound, 7-methyl-8-methylamino-10-(1'-D-ribityl)isoalloxazine, which is useful in the control of coccidiosis and protozoal and parasitic infections.

Another object of this invention is to provide a novel anticoccidial agent. Still another object of this invention is to provide novel feed compositions useful for the prevention and suppression of coccidiosis in poultry.

A further object of this invention is to provide a new and useful method for the control of coccidiosis in poultry which comprises administering to the poultry minor amounts of the anticoccidial substance of this invention.

A still further object of this invention is to provide a method for preparing the novel compound 7-methyl-8-methylamino-10-(1'-D-ribityl)-isoalloxazine.

These and further objects of this invention will become apparent or be described as the description thereof herein proceeds.

DESCRIPTION OF THE PREFERRED EMBODIMENTS

In accordance with this invention, coccidiosis in poultry is controlled or suppressed by administering to the poultry a non-toxic, anticoccidially effective quantity of the compound of the structural formula:

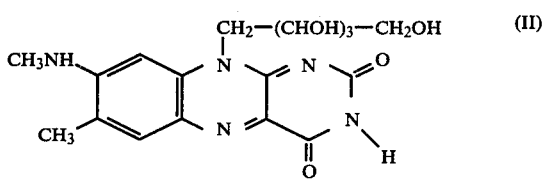

designated 7-methyl-8-methylamino-10-(1'-D-ribityl)-isoalloxazine.

In preparing the novel coccidiostat of this invention, a mixture of the starting materials, 8-chloro-7-methyl-10-(1'-D-ribityl)isoalloxazine, (I), and methylamine in DMF are heated in a sealed tube. The reaction time and temperature conditions are not unduly critical. The time of the reaction, however, decreases as the reaction temperatures increases. The reaction is most conveniently conducted between the temperature in the range of from about 0° C. to about 150° C. However, the preferred temperature is in the range of from about 80° C. to 100° C. for 30 min. to 1 ½ hours.

The relative proportions of the components of the reaction mixtue of the first step may vary over a relatively wide range. The reactants may be used in stoichiometric amounts, i.e., equal moles of the two reactants may be used, or a large excess of the amine may be used. The amount of the solvent used may also vary over a wide range. The solvent is used in a quantity sufficient to permit the reaction to proceed at a reasonable rate and facilitate isolation of the reaction product.

At the conclusion of the reaction, the reaction solution is evaporated to dryness under reduced pressure. The residue is recrystallized from water to give the desired 7-methyl-8-methylamino-10-(1'-D-ribityl)isoalloxazine.

The novel compound of this invention is orally administered to poultry for the control and prevention of coccidiosis. Any number of conventional methods are suitable for administering the coccidiostate of this invention to poultry, as for example, it may be given in the poultry feed or included in drinking water. The actual quantity of the coccidiostat administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not result in any undesirable effects.

A feed will typically contain from about 0.001 to about 0.25%, preferably from about 0.006 to about 0.05% by weight of the coccidiostat of this invention.

The optimum levels will naturally vary with the species of Eimeria involved, and can be readily determined by one skilled in the art. Levels of 7-methyl-8-methylamino-10-(1'-D-ribityl)isoalloxazine, the coccidiostat of this invention, in poultry feed of from about 0.0125% to about 0.025 by weight of the diet are especially useful.

The quantity or concentration of the novel coccidiostat of this invention in any mixture in which it is administered to the poultry will, of course, vary in accordance with the type of admixture utilized.

Of the various methods of administering the coccidiostat of this invention to poultry, they are most conveniently administered as a component of a feed composition. The novel coccidiostat may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

Suitable compositions also include feed premixed in which the active ingredient is present in relatively large amounts and which are suitable for addition into the feed either directly or after an intermediate dilution or blending step. Such compositions may also be added to the animals feed in the form of a top dressing. Typical carriers or diluents suitable for such compositions include for example, distillers dried grains such as corn distiller's dried grains and corn distiller's grains, corn meal and corn meal germ, citrus meal, fermentation residues, ground oyster shells, wheat shorts and wheat standard middlings, molasses solubles, corncob meal, edible bean mill feed, soyagrits, crushed limestone and the like. The active compound is intimately dispersed throughout the carrier by methods such as grinding, stirring, milling or tumbling. Compositions containing from about 0.1 to 50% by weight, especially from about 0.5 to 25% by weight of the compound 7-methyl-8-methylamino-10-(1'-D-ribityl)isoalloxazine are particularly suitable as feed premixes.

Examples of typical feed premixes containing 7-methyl-8-methylamino-10-(1'-D-ribityl)isoalloxazine dispersed in a solid inert carrier are:

| A. | 7-methyl-8-methylamino-10-(1'-D-ribityl)-isoalloxazine | 6.0 |
|---|---|---|
|  | Wheat standard middlings | 94.0 |
| B. | 7-methyl-8-methylamino-10-(1'-D-ribityl)-isoalloxazine | 10.0 |
|  | Corn distiller's dried grains | 90.0 |
| C. | 7-methyl-8-methylamino-10-(1'-D-ribityl)-isoalloxazine | 20.0 |
|  | Corn germ meal | 30.0 |
|  | Corn distiller's grains | 50.0 |

In accordance with an additional embodiment of this invention, novel and highly effective, broad spectrum anticoccidial compositions are provided by mixing the 7-methyl-8-methylamino-10-(1'-D-ribityl)-isoalloxazine with one or more other anticoccidial agents. With such combinations, therefore, it is possible to achieve very effective controls of mixed coccidial infections. It is thus possible to achieve optimum results with much smaller amounts of each coccidiostat than if only one member of the mixture was used alone.

Among the coccidiostats which may be used in combination with 7-methyl-8-methylamino-10-(1'-D-ribityl)isoalloxazine are amprolium, monensin, clopidol, nicarbazin, ethopabate, zoalene, 3,5-dinitrobenzamide, buquniolate and 9-(2-chloro-6-fluorobenzyl)-adenine. All or any of these, as well as others not given in this representative listing, may be combined with 7-methyl-8-methylamino-10-(1'-D-ribityl)isoalloxazine to give highly potent coccidiostat compositions.

The feed may be supplemented by up to 100% of the normal level (3 to 5 ppm) of riboflavin to decrease the toxicity of 7-methyl-8-methylamino-10-(1'-D-ribityl)isoalloxazine to the chickens without changing its effectiveness against coccidia.

The compound of this invention has value in the control of trypanosomiasis in domesticated animals, particularly cattle. For this purpose, it may be administered orally with an ingestible carrier as a component of the animal feedstuff, in the drinking water, in salt blocks and in unit dosage forms such as boluses and drenches. The amount of active ingredient required for optimum control of trypanosomiasis varies in accordance with such factors as the species of animal to be treated, the species of infecting parasite, the severity of infection, and whether the compound is employed therapeutically or prophylactically. In general, the compound, 7-methyl-8-methylamino-10-(1'-D-ribityl)isoalloxazine, when administered orally to domestic animals in daily doses of from about 0.1 mg. to about 500 mg. per kilogram of animal body weight is highly effective in controlling trypanosomiasis without intolerable toxic effect. When these compounds are to be employed as therapeutic agents, good results are obtained when the animals are fed a daily dose of from about 5 mg. to about 500 mg. and preferably 15 mg. to 250 mg. per kilogram of body weight.

In employing 7-methyl-8-methylamino-10-(1'-D-ribityl)isoalloxazine as an antimalarial, the compound is preferably administered orally. Oral dosage forms such as capsules, tablets or powders in which the drug is intimately admixed with a non-toxic solid pharmaceutically acceptable carrier or diluent vehicle are preferred. However, liquid formulations such as syrups, suspensions or elixirs may be used if desired. The compound may also be administered parenterally or intravenously in which case they may be formulated as a solution or suspension in sterile physiologic saline.

The preferred dose level for controlling malaria in humans of 7-methyl-8-methylamino-10-(1'-ribityl)isoalloxazine is from about 10-2000 mg. per day. As will be understood and appreciated by those skilled in this art, the preferred or optimal dose will depend to some extent upon the species of malaria being treated, the type of treatment being used, i.e., prophylactic or therapeutic. Selection of optimum dose is made without difficulty by a clinician skilled in this art. For example, treatment of acute attacks requires higher and more frequent doses whereas in suppressive or prophylatic therapy lower doses are used but over a longer period of time. When 7-methyl-8-methylamino-10-(1'-D-ribityl)isoalloxazine is used against falciparum malaria, oral doses of about 100–1000 mg./day for 1–10 days give good results in treating an acute attack; for preventive therapy the regimen is continued for up to two weeks after the acute stage. Similar treatment is useful against acute attacks of vivax and malariae malaria, but with these strains prophylactic or suppressive therapy is continued for a much longer period of time.

The following non-limiting examples will serve to further illustrate the instant invention.

EXAMPLE 1

A glass tube was charged with 300 mg. 8-chloro-7-methyl-10-(1'-D-ribityl)isoalloxazine, 3 ml. methylamine in 3 ml. DMF and sealed. The sealed tube was heated at 90° C. for 1 hour. The dark red reaction mixture was evaporated under reduced pressure and the residue recrystallized from water to give 7-methyl-8-methylamino-10-(1'-D-ribityl)-isoalloxazine, m.p. 315°–320° C. (dec.).

Calc. for $C_{17}H_{21}N_5O_6$: C, 52.17; H, 5.41; N, 17.90.
Found: C, 52,53; H, 5.50; N, 17.61.

Although this invention has been described in relation to specific embodiments, it will be apparent that obvious modifications may be made by one skilled in the art without departing from the intended scope thereof as defined by the appended claims.

What is claimed is:

1. The compound of the structural formula:

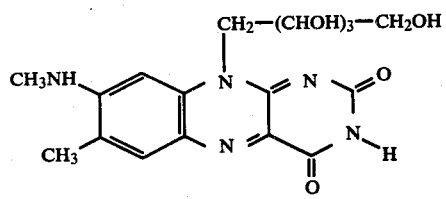

2. A pharmaceutically acceptable composition for the treatment of coccidiosis comprising an effective amount of the compound of the structural formula:

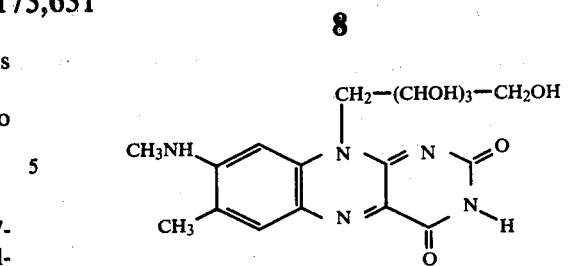

in poultry feed.

3. A composition according to claim 1 wherein said compound comprises from 0.001% to 0.25% by weight of said composition.

4. A composition according to claim 3 wherein said compound comprises from 0.006% to 0.05% by weight of said composition.

5. A composition according to claim 2 wherein said composition is a feed premix and said compound comprises from 0.1% to 50% by weight of the premix.

6. A composition according to claim 5 wherein said compound comprises from 0.5% to 25% by weight of said premix.

7. A composition for the treatment of malaria comprising an effective amount of the compound of the structural formula:

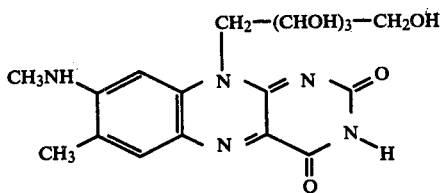

in a non-toxic pharmaceutically acceptable carrier.

* * * * *